United States Patent [19]

Beatty et al.

[11] Patent Number: 5,325,443
[45] Date of Patent: Jun. 28, 1994

[54] VISION SYSTEM FOR INSPECTING A PART HAVING A SUBSTANTIALLY FLAT REFLECTIVE SURFACE

[75] Inventors: John M. Beatty, Murrysville; Edward C. Borgoyn, North Braddock, both of Pa.

[73] Assignee: Westinghouse Electric Corporation, Pittsburgh, Pa.

[21] Appl. No.: 549,570

[22] Filed: Jul. 6, 1990

[51] Int. Cl.⁵ .............................................. G06K 9/56
[52] U.S. Cl. ........................................ 382/8; 382/49; 364/552; 356/237
[58] Field of Search .................... 382/8, 49; 364/552; 358/106, 101; 356/237

[56] References Cited

U.S. PATENT DOCUMENTS

| | | | |
|---|---|---|---|
| 4,395,698 | 7/1983 | Sternberg et al. | 382/41 |
| 4,500,202 | 2/1985 | Smyth | 356/237 |
| 4,519,041 | 5/1985 | Fant et al. | 364/552 |
| 4,561,104 | 12/1985 | Martin | 382/8 |
| 4,733,229 | 3/1988 | Whitehead | 340/747 |
| 4,811,410 | 3/1989 | Amir et al. | 382/8 |
| 4,831,641 | 5/1989 | Niemi | 382/8 |
| 4,868,651 | 9/1989 | Chou et al. | 358/111 |
| 4,929,845 | 5/1990 | Amir et al. | 250/561 |
| 4,963,036 | 10/1990 | Drisko et al. | 382/50 |
| 4,972,494 | 11/1990 | White et al. | 382/8 |

Primary Examiner—David K. Moore

[57] ABSTRACT

The two sides of a flat panel are inspected in successive inspection stations each of which includes a camera having a linear array of CCD elements which generates an image line-by-line from a stripe of light reflected by one flat surface of the panel as the panel is conveyed through the inspection station. The signals representing images of the two faces of the panel are independently digitized and stored in separate pixel arrays of gray-scale values. The images are queued for filtering followed by processing by a single image processing board which generates a table of hits, identified as pixels having gray-scale values which breach preselected thresholds. Sections of the stored pixel array are transmitted sequentially to the image processing board which has a frame size smaller than the stored array, with the frame sized sections overlapping as required to confine the pixels processed to those inside the edges of the panel image. A microprocessor analyzes the hits identified by the image processing board and generates a reject signal if the density of hits exceeds a limit. The microprocessor also associates hits by proximity into blobs and rejects the panel if a weighted count of hits in any blob exceeds predetermined criteria.

17 Claims, 11 Drawing Sheets

VISION SYSTEM FOR INSPECTING A PART HAVING A SUBSTANTIALLY FLAT REFLECTIVE SURFACE

BACKGROUND OF INVENTION

1. Field of Invention

This invention relates to a system for visually inspecting flat reflective parts such as metal panels for defects, which may include scratches, gouges, holes inclusions and such, by scanning the panel with a stripe of light, recording the gray-scale values of reflected light for an array of pixels covering the panel, and processing the gray-scale values for the array of pixels using high speed vision processing equipment to identify the defects. More particularly, the invention is directed to such a system in which modular vision processing boards with limited area coverage are used to inspect larger panels on-line and in which the data indicative of a defect is reduced to speed processing.

2. Background Information

Many flat parts such as for example copper laminate panels used in making printed circuit boards must be inspected after manufacture to identify defective units. Typical defects in these copper laminate panels include scratches, gouges, dents over certain dimensions, pinpoint holes and inclusions, any of which could impair the performance of a printed circuit board using such a panel. The presence of a few minor scratches, dents, et cetera may be tolerated, however, a large number of even such minor blemishes is cause for rejection. To date, the inspection of such panels has been accomplished by workers visually scanning each panel. Thus, inspection has been labor intensive and, therefore expensive. It is also prone to variability from one inspector to another.

It is therefore an object of the invention to provide a reliable, reasonably priced automated system for inspecting panels and other flat reflective parts.

It is a more specific object of the invention to provide such an automated inspection system which generates a pixel array of gray-scale values of light reflected from the inspected panel and which utilizes modular vision processing apparatus to generate data representing selective defects in the panels.

It is a further object of the invention to provide such system in which modular vision processing equipment with limited area coverage can be used to inspect panels of larger area.

It is an additional object of the invention to provide such a system incorporating techniques which reduce the data indicative of the selected defects to reduce processing time and the capacity of the apparatus required to perform the inspection on-line.

SUMMARY OF THE INVENTION

These and other objects are realized by the invention which is directed to a vision system for inspecting parts having substantially flat reflective surfaces in which a pixel array of gray-scale values of light reflected from the reflective surfaces of the part are evaluated on-line to detect the presence of various defects such as scratches, gouges, holes, inclusions and such. The gray-scale values of the pixel array are compared to threshold values by an image processing board which generates a table of hits identifying the pixels having gray-scale values which breach the thresholds. The gray-scale values are filtered before the evaluation to increase contrast which reduces the number of hits and therefore the amount of processing required. In addition to rejecting a part having a total number of hits which exceeds a selected value, the system associates hits by proximity into blobs and also rejects a part having blobs containing more than a selected number of hits. In the preferred embodiment of the invention, the image processing board compares the pixel gray-scale values to multiple thresholds and rejects a part based upon a weighted count of hits in a blob.

As another aspect of the invention, the pixel processing board has a frame size smaller than the portion of the pixel array covering the flat reflective surface. In accordance with the invention, successive sections of the pixel array covering the flat reflective surface are transferred to the pixel processing board until the entire image of the surface has been processed. In order to reduce the number of hits and therefore the processing burden, only gray-scale values for pixels within the flat reflective surface are passed to the pixel processing board for processing. In the exemplary system, only the area of the surface more than one quarter inch in from the edges of the part is evaluated. Where the frame size of the pixel processing board is not a whole multiple of the portion of the pixel array covering the flat reflective surface, the frame sized sections of the array transferred to the pixel processing board are overlapped to maintain the total coverage processed to that of the flat reflective surface. Redundant hits in the overlapping portions of the frame sized sections of the pixel array are eliminated.

As applied to inspecting panels having two flat reflective surfaces, the panels are passed through two successive inspection stations each generating a set of pixel gray-scale values for one flat reflective surface. Separate pixel arrays for each surface are generated independently. The images are queued for sequential processing by a single pixel processing board. Since each pixel array is larger than the frame size of the pixel processing board, and therefore must be processed in sections, the features of the invention, such as only processing the portion of the reflective surfaces more than a certain distance from the edges, overlapping the frame sized sections to remain within those borders, filtering of the raw gray-scale values, and associating hits into blobs, all contribute to reducing the processing burden so the inspection can be made on-line with reasonably priced equipment.

BRIEF DESCRIPTION OF THE DRAWINGS

A full understanding of the invention can be gained from the following description of the preferred embodiment when read in conjunction with the accompanying drawings in which.

DESCRIPTION OF THE PREFERRED EMBODIMENTS

Figure 1:
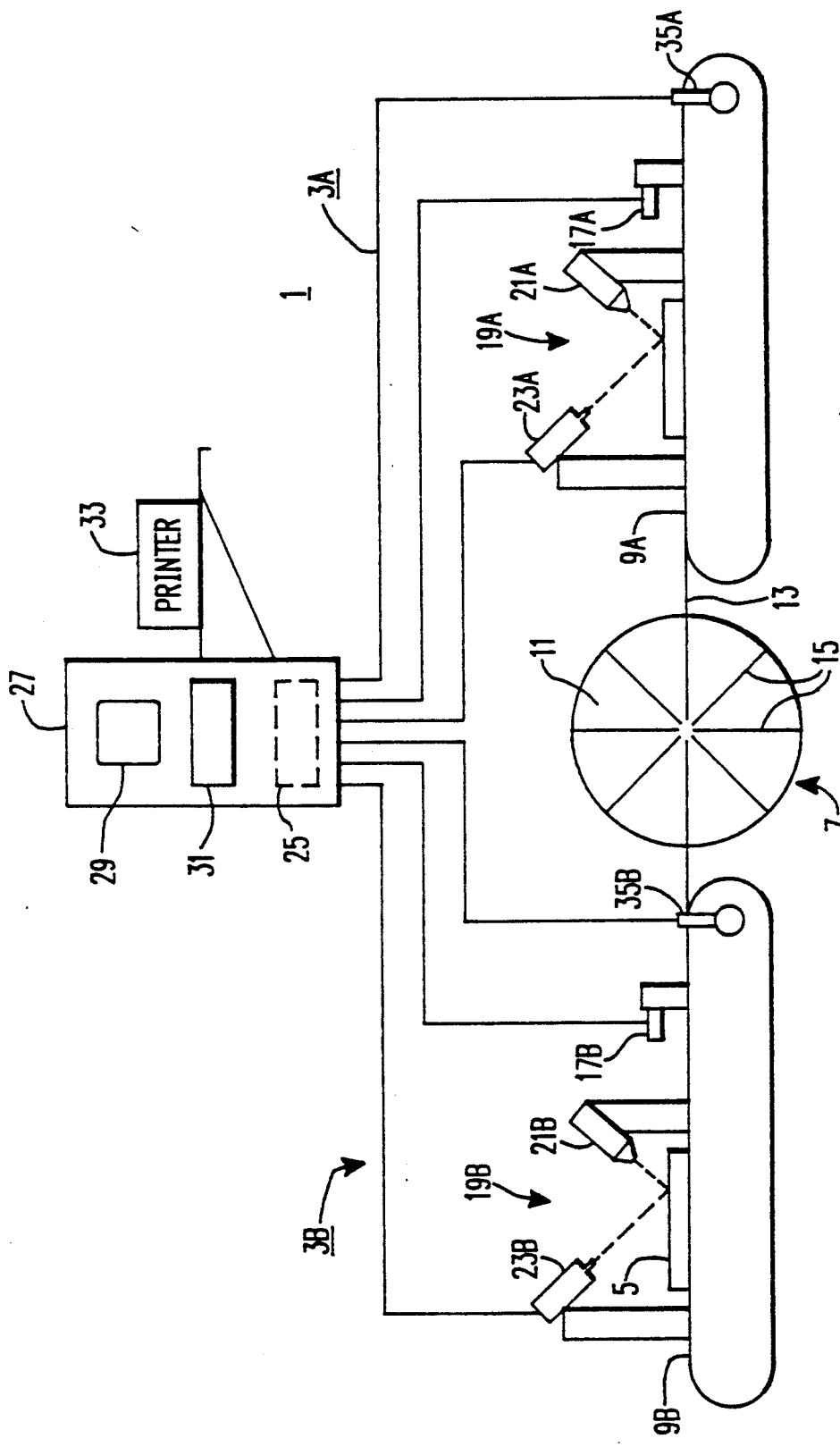
FIG. 1 is a general schematic diagram illustrating a system in accordance with the invention for inspecting flat panels.

Referring to the drawings, the invention will be described as applied to a system 1 for inspecting copper laminate panels used for making printed circuit boards. However, it will become clear to those skilled in the art that the invention has broad application to the inspection of a wide variety of flat parts in which defects or other features to be detected have a reflectivity detectably different from the remainder of the flat surface of the part.

The system 1 includes two inspection stations 3a and 3b, one for inspecting each face of the copper laminate panels 5. An inverting transfer station 7 turns the panels 5 over after a first side has been inspected at the station 3a for inspection of the second face at the station 3b.

Each of the inspection stations 3a and 3b includes a belt conveyor 9a and 9b, respectively. The panels 5 are placed on the conveyor belt 9a by a feeder apparatus (not shown) and transferred from the conveyor belt 9a to the conveyor belt 9b by the inverting transfer station 7. The inverting transfer station 7, which is known, includes a number of axially displaced disks 11 which are interleafed with roller sections of a roller conveyor 13. The disks 11 have a number of angularly displaced slots 15 which receive the panels 5 from the conveyor 9a. The disks 11 are indexed in sychronism with operation of the conveyors 9a and 9b to invert the panels while transferring them from the first inspection station 3a to the second inspection station 3b.

As a panel 5 is carried along by the conveyor belt 9a or 9b, the leading edge of the panel is detected by a sensor 17a or 17b, respectively. In the exemplary system, optosensors are used for the sensors 17a and 17b. The conveyors 9a and 9b advance the panels 5 past optical data acquisition systems 19a, and 19b. These optical acquisition systems include fluorescent strip lamps 21a and 21b which direct stripes of light onto the moving panels oriented transversely to the direction of travel of the panels. The stripes of light strike the panels at an angle of incidence which is less than 90° and are reflected to cameras 23a and 23b. Each camera has a single row of 2048 CCD (charge coupled device) elements focused on an area extending the full width of the panel 5 by 12 mils in the direction of travel. As a panel 5 traverses a camera's line-of-sight, the video information for an image of the panel is built up line-by-line. This video information is digitized and stored in a large memory in a vision processor housed in a cabinet 27. The cabinet 27 also houses a video monitor 29, a data entry terminal 31 for operator interface, and a printer 33 for generating hard copies of defect reports generated by the system.

Each of the inspection stations 3a and 3b also includes an optical encoder 35a and 35b attached to the drive roll of the associated conveyor 9a and 9b, respectively. These optical encoders are used to measure belt speed indirectly through shaft position. As the leading edge of a panel 5 passes under the optosensor 17a or 17b which is installed at a fixed distance in front of the line-of-view of the camera 23a or 23b, a pulse is generated. An encoder reading is taken immediately after the panel triggers the optosensor. A second reading is taken at a subsequent time when the panel edge is near the view-line but not past. The difference in encoder readings is proportional to the average speed for the time of travel. From the computed speed and position, time of arrival of the panel at the view line is computed. At that time, the video processor 25 is enabled to begin inputting data from the camera 23a or 23b.

Figure 2:
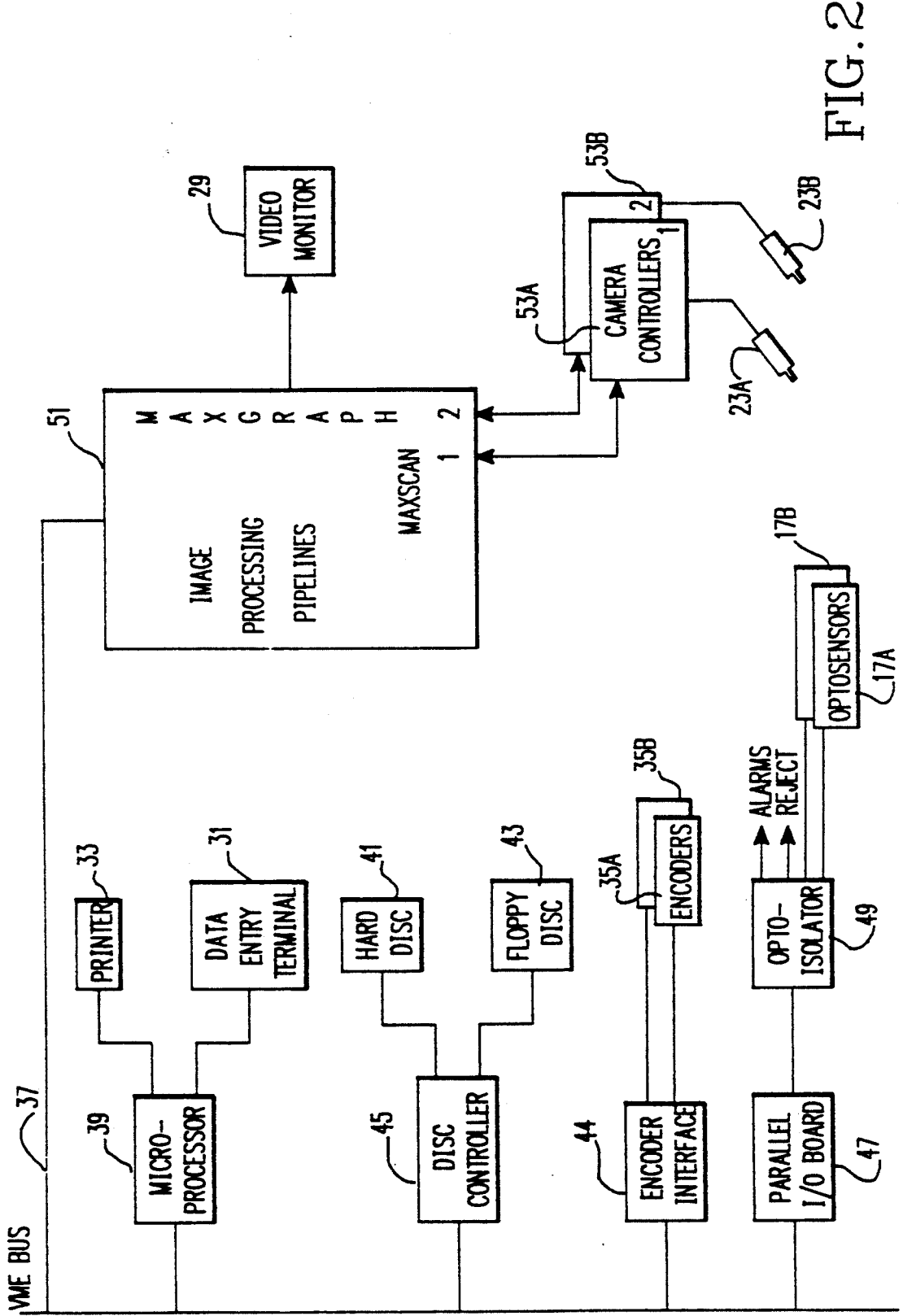
FIG. 2 is a schematic diagram of a vision processor which forms part of the system illustrated in FIG. 1.

A block diagram of the video processor 25 which is housed in the cabinet 27 is illustrated in FIG. 2. The various components of the system are interconnected by a VME bus 37. The processor includes a microcomputer 39, the data entry terminal 31 and the printer 33, a hard disk memory 41 and a floppy disk memory 43 and their controller 45, an encoder interface 44 which provides inputs from the optical encoders 35A and 35B, and a parallel input/output board 47 which also performs timing functions. The input/output board 47 interfaces with an optoisolator panel 49 which provides isolated signals from the optosensors 17a and 17b. The input/output board 47 also provides through the optoisolator panel 49 contact outputs for alrms generated by the system and signal for controlling a reject station (not shown) which diverts rejected panels downstream of the conveyor 9b.

The video processor 25 also includes image processing pipelines 51. These image processing pipelines control the cameras 23a and 23b and receive video signals from these cameras through camera controllers 53a and 53b. As will be discussed, the image processing pipelines 51 process the raw video data for transmission over the VME bus 37 to the microprocessor 39. The image processing pipelines also supply video signals to the monitor 29.

Figure 3:
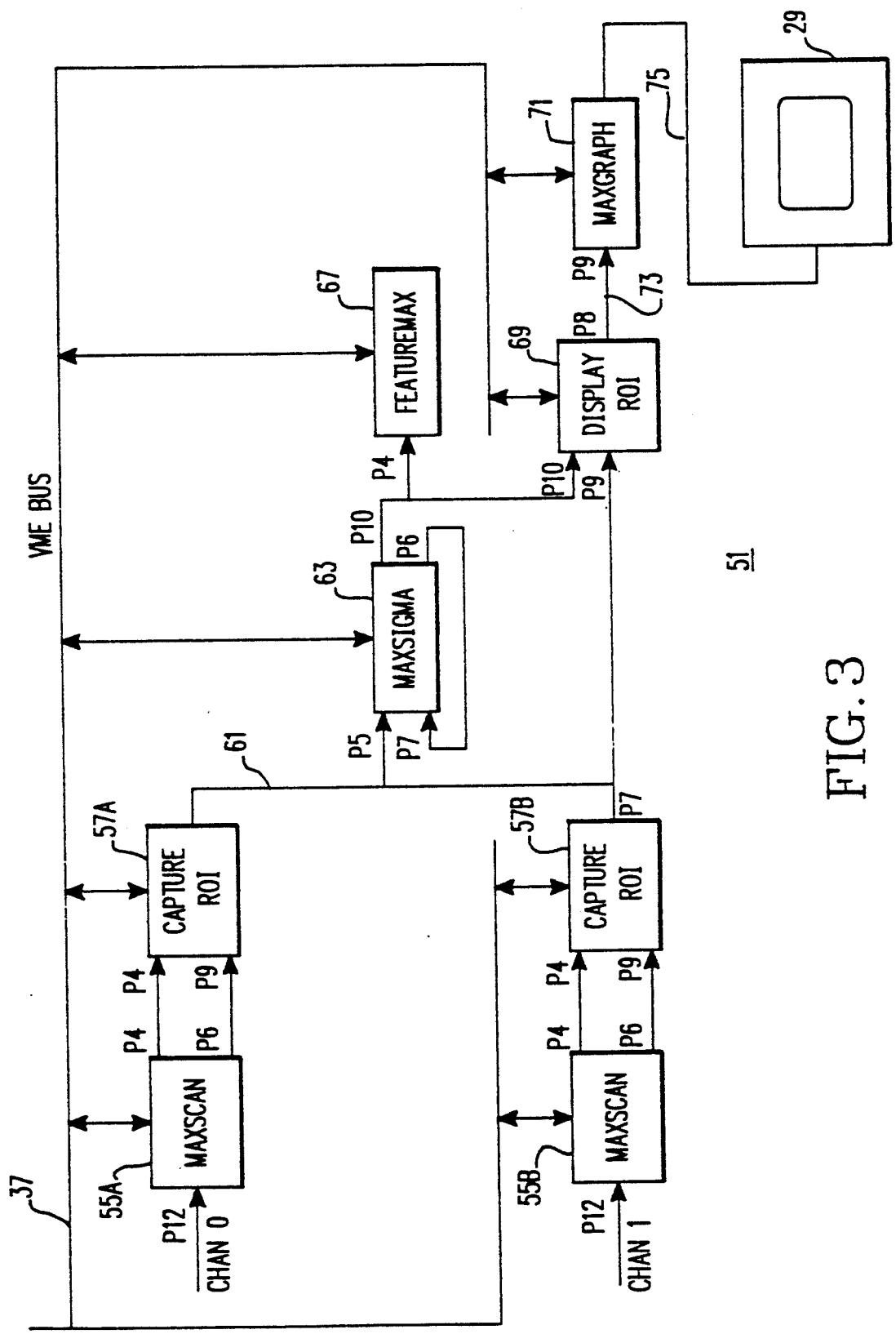
FIG. 3 is a schematic of image pipelines which form part of the vision processor of FIG. 2.

The image processing pipelines 51 are illustrated in block diagram form in FIG. 3. These pipelines include a number of special purpose processors, all residing on the VME bus 37. In the exemplary system, the special purpose processors are all image processing boards manufactured by Data Cube, Inc. Each of the cameras 23a and 23b sweep the elements of the linear array at a rate of 1000 lines per second to generate analog electrical signals identified in FIG. 3 as channel zero and channel 1 signals, respectively. These analog video signals are applied to line scan interface boards (MAX-SCAN) 55a and 55b which digitize the analog signals for storage in Capture ROI (region of interest) modules 57a and 57b. Each of the capture ROI boards 57a and 57b has a memory array which is 2000 by 4000 pixels with 8-bit resolution. Since the largest panel inspected by the system generates data for an array 2000 pixels by 1500, each of the Capture ROI boards 57a and 57b can store data for two separate panels. Thus, while data is being read out for a previously imaged panel, data can be read in for the next panel.

The images captured by the two cameras are queued for transmission over a line 61 in RS-170 video format to a MAX-SIGMA board 63 which is configured as a Laplacian filter. The filtered output of the MAX-SIGMA board 63 is transmitted over the line 65 also in RS-170 video format to a FEATUREMAX board 67 which is a multi-level threshold detector. The FEATUREMAX board can compare the filtered grayscale values to a number of positive and negative thresholds. Since the defects to be detected have a lower reflectivity than the unblemished portions of the panels, the negative thresholds are used. The FEATUREMAX board 67 generates a table of hits identifying the pixels having gray-scale values below the selected negative thresholds. The hit table records the x, y coordinates of the hit and includes for each hit two bits indicating the lowest threshold breached. The Laplacian filter function applied by the MAX SIGMA board 63 enhances the contrast of the gray-scale values of the captured image, and therefore enhances the definition of the edges of the defects. The thresholds applied by the FEATUREMAX board 67 are then selected to detect these edge features which reduces the number of hits and therefore the amount of data that must be processed. The table of hits generated by the FEATUREMAX board provides the basis upon which the acceptance/rejection decision is made by the microprocessor 39.

For debugging purposes, a Display ROI board 69 selects among the raw gray scale data on lines 61 from a selected one of the Capture ROI boards 57a or 57b, or the filtered output of the MAX SIGMA board 63 on the lines 65 and sends the resulting image to a MAX-GRAPH board 71 over lines 73. The MAX-GRAPH board 71 can superimpose over the image received from the Display ROI the processed hit data received over the VME bus 37 from the digital processor 39. The composite image is then passed over lines 75 to the display monitor 29.

A novel feature of the invention lies in the implementation of the threshold processing by the FEATUREMAX board 67. The size and desired resolution of the image dictates that the images of the panels 5 require as many as approximately 2000 pixels in the cross web direction and approximately 1500 pixels in the down web direction for the largest panel which is 24 inches by 18 inches. The FEATUREMAX board 67, however, is limited to processing frames of 512 cross web pixels by 483 down web pixels. In order to process the entire panel image with the desired resolution, the FEATUREMAX board 67 is used to successively process a multiplicity of frames covering the panel 5. It is also important, in accordance with the invention, to avoid generating a large number of threshold crossings associated with the edge of the panel and the background since this would increase the processing load on the microprocessor which receives the hits from the FEATUREMAX board. Therefore, in accordance with the invention, threshold processing is restricted to processing only pixels on the board. In the exemplary system, only pixels more than 0.25 inches from the edges of the panel are processed. This is not a drawback since generally components are not placed closer than one quarter inch from the edge of a printed circuit board in any event.

Figure 4:
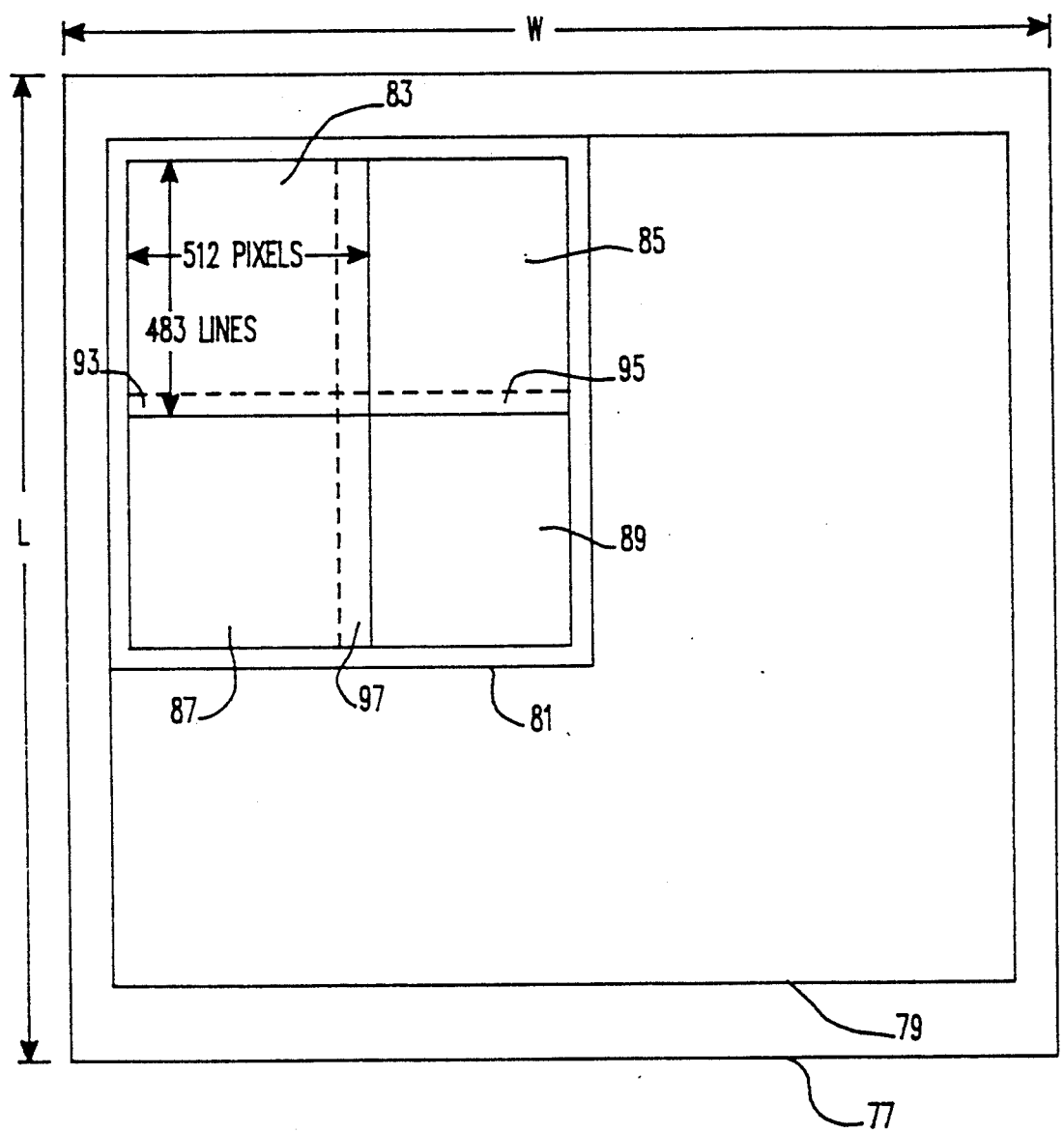
FIG. 4 is an illustration of the manner in which the image pipelines illustrated in FIG. 3 process data for a large panel using modular units having a smaller frame size.

The scheme for utilizing the FEATUREMAX board with a frame size of 512 by 483 pixels to inspect large panels is illustrated in FIG. 4. The array 77 stored in the Capture ROI boards 59 is 2048 pixels wide and covers an area 26.6 inches in width W thereby providing a resolution of 0.013 inches at 77 pixels per inch. The array 77 is also 2048 pixels high representing a length L of 24.6 inches along the conveyor thereby providing a resolution of 0.012 inches for each pixel at 83.3 pixels per inch. In the exemplary system, the largest panels inspected are 24 inches by 21 inches as represented by the outline 79 superimposed on the capture ROI array 77. The smallest panel inspected by the exemplary system is 12 inches by 12 inches as represented by the outline 81 in FIG. 4. The feeder system left justifies the panels as they are loaded onto the conveyor 9a so that they are all spaced a fixed distance from the left margin in the Capture ROI array 77. In addition, the optosensor and encoder are used to initiate capture of the data as described so that the data for all of the panels starts at a fixed distance from the top of the Capture ROI array.

Even for the smallest panel to be inspected by the exemplary system, the number of pixels needed to cover the panel exceeds the frame size of the FEATUREMAX board. In accordance with the invention, successive sections, such as the sections 83, 85, 87 and 89, each equal in size to the 512 by 483 pixel frame size of the FEATUREMAX board are successively transferred to the FEATUREMAX board for processing. As previously mentioned, and in order to reduce the processing required, only sections more than one quarter inch dimension B in FIG. 4, from the edges of the panel image are transferred to the FEATUREMAX board. The successive sections, each equal to a frame of the FEATUREMAX board, are transferred to the FEATUREMAX board until the entire panel has been processed. When less than a full frame remains to be processed at the right and at the bottom, the frame is moved left or up to within one quarter inch of the right and/or the bottom respectively of the image, thus, overlapping a previously processed area as shown at the left side 91 of the section 85, the upper portion 93 of the section 87 and by the portions 95 and 97 of the section 89. Any resultant redundancy is eliminated as will be seen in the processing of the data. Since the data is generally extremely sparse, this does not burden the processing.

In inspecting panels for defects, the digitized video data are entered into the Capture ROI boards 57a and 57b in real time as the panels move past the optical data acquisition system lines of sight. This data acquisition is effected independently for the two channels, channel zero and channel one, inspecting opposite sides of the panels at the inspection stations 3a and 3b, respectively.

Figure 5:
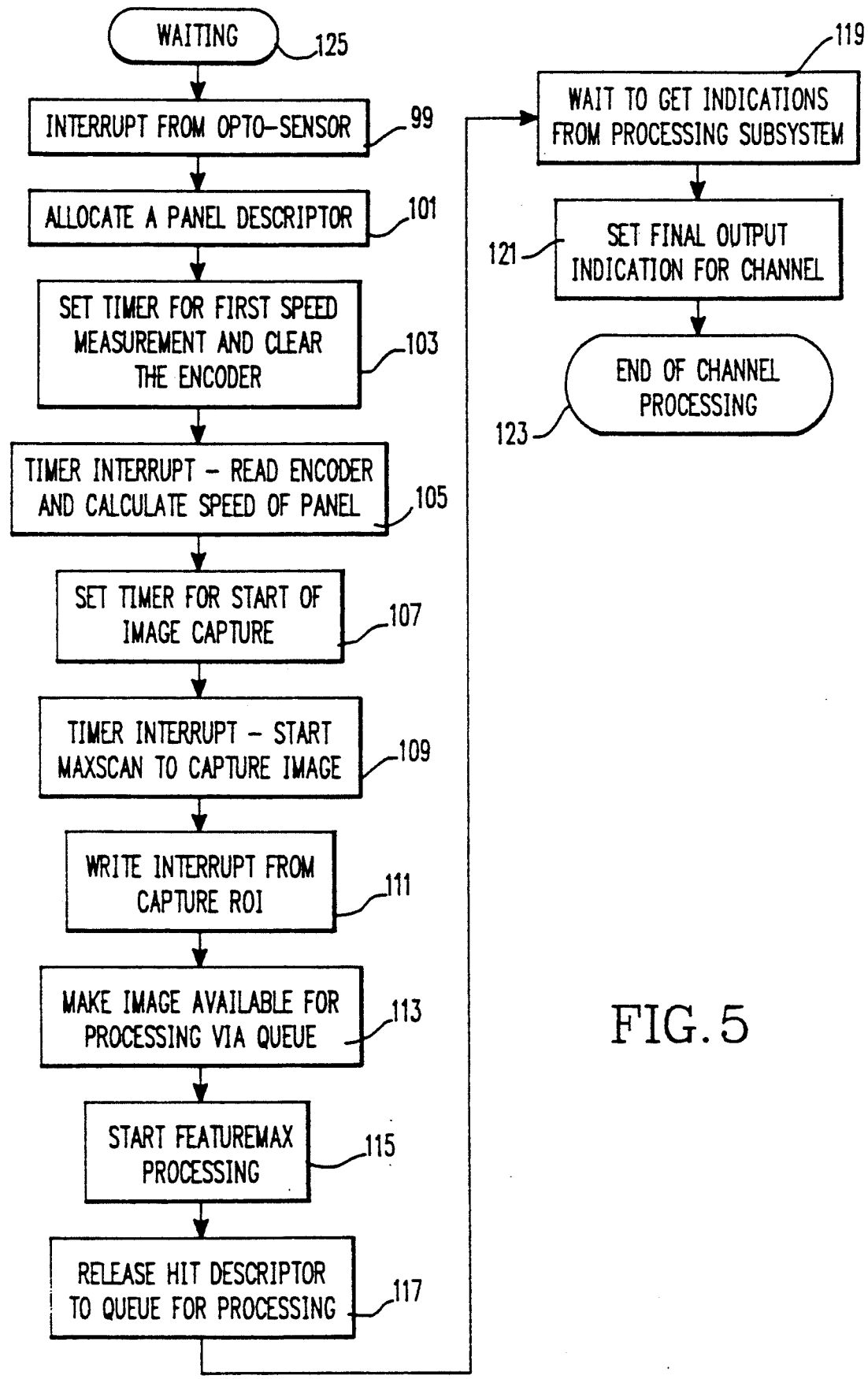
FIGS. 5 through 8 and 9a and 9b are flow charts of a suitable program used by the system illustrated in FIGS. 1-3.

A flow chart for a suitable program implemented by the microprocessor 39 to process one channel for a panel is illustrated in FIG. 5. When, as indicated at 99 in the flow chart, an interrupt from the optosensor 17a or 17b reports that a panel is approaching the camera line of sight, the panel is allocated a descriptor at 101 for identification. The timer in the input/output timer board 47 is then set for the first speed measurement and the count generated by the encoder 35a or 35b is cleared all as indicated at 103. When the timer times out, the encoder is read and used to calculate the speed of the panel on the conveyor as indicated at 105. The timer is then set for the calculated time at which the panel will reach the camera line of sight as indicated at 107. When this interval has expired, a signal is sent to MAX-SCAN, 55a or 55b, to initiate image capture as indicated at 109. The capture ROI board for the channel 57a or 57b generates an interrupt when the image capture has been completed. Upon receiving this interrupt at 111, the captured image is made available for processing by placing it in a queue at 113. As will be observed, one FEATUREMAX board processes the images generated by both of the channels. When FEATUREMAX is available, FEATUREMAX processing of the image is initiated at 115. As discussed, the FEATUREMAX board generates an array of hit tables indicating the number of pixels having gray-scale values which are below selected thresholds, the addresses of those pixels and the lowest threshold breached. Upon the completion of processing by FEATUREMAX, the hit descriptor identifying the array of tables of hits for the processed image is queued for processing at 117. The results of this processing of the hits, such an indication that the panel is to be rejected, is received at 119 and the final output for the channel is set at 121. For instance, if the indication received from the processing subsystem is that the panel is to be rejected, the output is set to cause the panel to be diverted downstream. This completion of processing of the channel is indicated 123 and the program waits at 125 for another panel to approach the inspection station.

Figure 6:
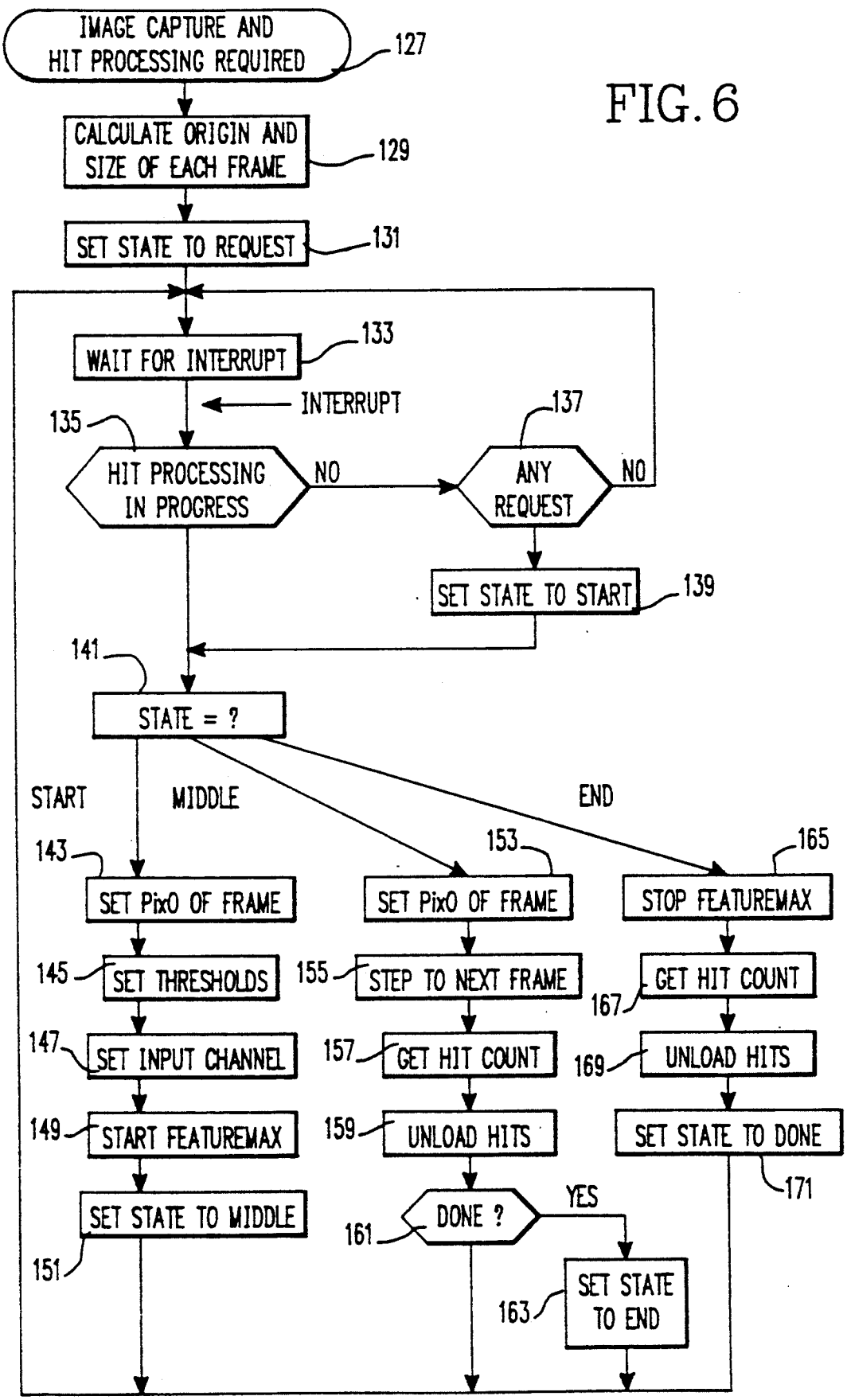

When FEATUREMAX processing is initiated at 115 in FIG. 5, the routine shown in FIG. 6 is run. When this routine is called at 127, the origin and size of each of the sections of the pixel array stored in the capture ROI memory and any overlaps are calculated at 129 and a state flag is set to REQUEST at 131. The system then waits for an interrupt from the Capture ROI board as indicated at 133. The Capture ROI board generates this interrupt at the beginning of the vertical blanking interval. Since FEATUREMAX processing is just being initiated, hit processing will not be in progress when checked at 135. Since there is a request at 137, the state flag is set to start at 139, so that when the state is checked at 141, the program will set the pixel index to the initial index of the frame at 143, and set the thresholds at 145. As mentioned, the FEATUREMAX board is provided with four thresholds against which it compares the gray scale value for each pixel in the frame being processed. With the thresholds set, the input channel to be processed is set at 147 and the FEATUREMAX board is started at 149. The FEATUREMAX board then compares the gray scale value for each of the pixels in the frame to the four thresholds and stores the hits, that is the pixels having a gray-scale value below any of the thresholds, in a hit table. The state flag is then set to MIDDLE at 151 and the program waits for the next interrupt. Upon receiving the next interrupt from the Capture ROI board, the pixel index is then set to the initial pixel of the next frame at 153 and the next frame is processed by FEATUREMAX at 155. While this is occurring, the hit count for the previous frame and the hits for the previous frame are transmitted to the microprocessor at 157 and 159, respectively. If there are more frames to be processed as determined at 161, the state remains MIDDLE and the additional frames are processed in a similar manner. When all of the frames required to process the larger array stored in the capture ROI for the panel have been processed by FEATUREMAX, the state is set to END at 163. Following the next Capture ROI interrupt FEATUREMAX operation is terminated at 165. The hit count for the last board is transmitted at 167 and the hits for the last frame are transmitted at 169 before the state is set to DONE at 171.

Figure 7:
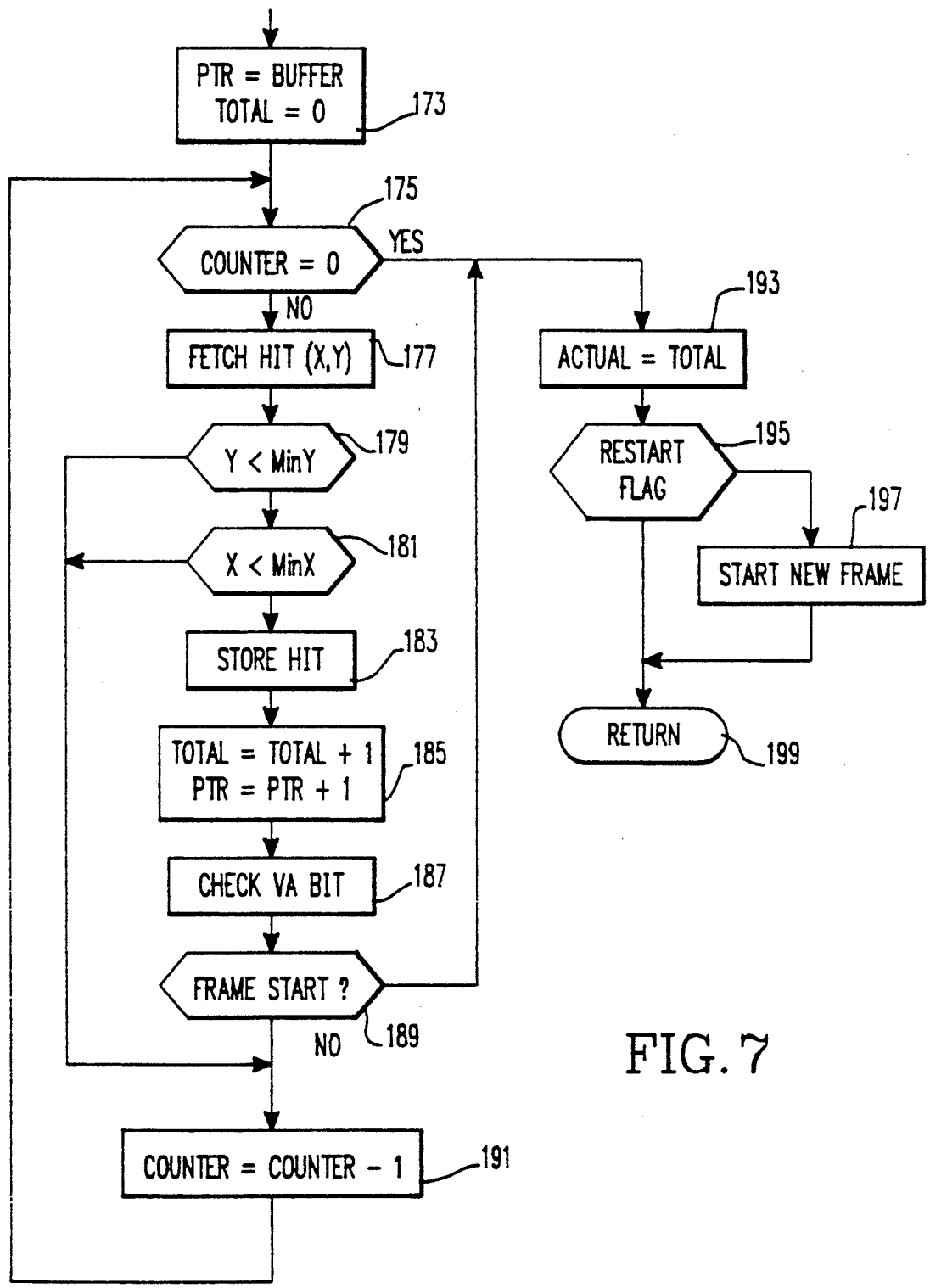

The flow chart for a routine for unloading hits from the FEATUREMAX board to the microprocessor as called for at 109 and 169 in the flow chart of FIG. 6 is illustrated in FIG. 7. This unloading of the x and y coordinates of the hits and the thresholds breached must be implemented very rapidly and is accomplished during the vertical blanking interval of the Capture ROI board from which the data is being processed. As indicated at 173 in FIG. 7, a POINTER is set to the location in the memory of the microprocessor at which storing of the hit table is to be initiated, and a parameter TOTAL, which tracks the number of hits transferred to computer memory, is initialized to zero. A loop is then entered at 175 to transmit the hit table, with the number of hits to be transferred equal to the count generated by the FEATUREMAX board of the number of hits recorded in the hit table for the frame being processed. Until that total number of hits has been transmitted, an entry from the hit table is fetched at 177. In order to eliminate double inclusion of hits for overlapping sections of the Capture ROI pixel array, the microprocessor in defining the frame sized sections of the Capture ROI to be successively processed by the FEATUREMAX board, specifies minimum x and y coordinates of the frame to eliminate the overlap. Accordingly, if the x and y coordinates of the hit under consideration are not in the overlap area as determined at 179 and 181, the data for the hit is copied to the computer memory at 183. The parameter TOTAL and the POINTER are then incremented at 185. The video active, VA, bit generated by the Capture ROI board is then checked at 187. If this video active bit indicates that the Capture ROI board is still in the vertical blanking interval, than COUNTER is decremented at 191 and the additional entries in the hit table are transmitted to microprocessor memory in a similar manner. When all of the hits in the hit table have been transmitted as determined at 175, or the Capture ROI has begun to transmit a new frame of data to the filter as determined at 189, then a parameter ACTUAL indicating the number of hits actually transferred to the microcomputer is set equal to total at 193. If a RESTART flag indicating that there are additional frames of the Capture ROI image to be processed is set, as determined at 195, then a START NEW FRAME flag is set at 197 before the routine returns to the calling program at 199.

Figure 8:
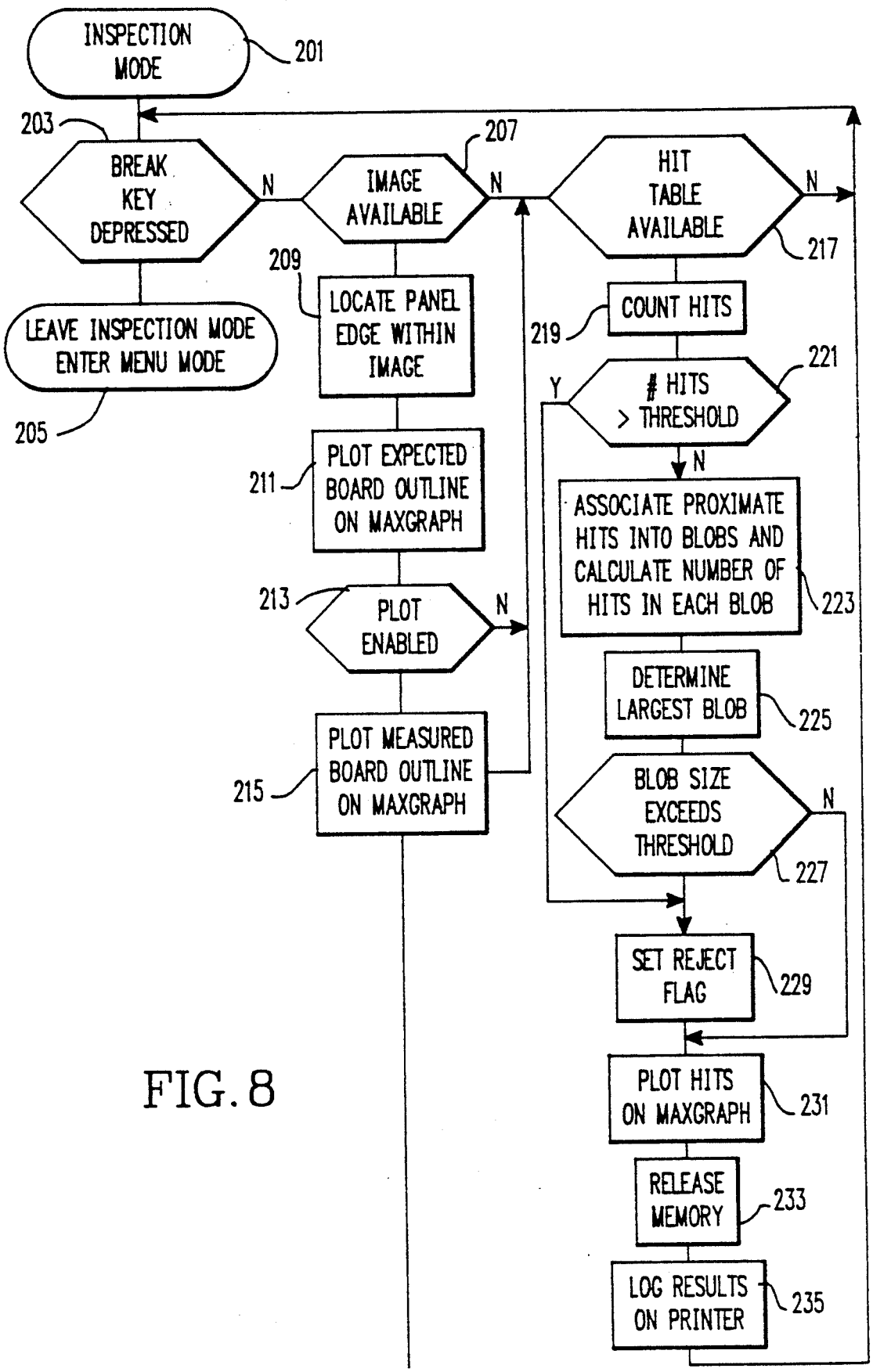

A flow chart for image and hit table processing by the microprocessor 39 is illustrated in FIG. 8. With the system in the inspection mode as indicated 201, if a break key is depressed as determined at 203, indicating that the operator is interfacing with the system, the inspection mode is exited at 205 for the menu mode. If the operator is not interfacing with the system, a determination is made at 207 if an image is available for processing. When an image is available, the edge of the panel within the image is located at 209. This location of the panel edge is then used to plot the expected board outline on the MAX-GRAPH board 71, which it will be recalled, is used to generate the display on the monitor 29. If the operator has selected plot enable as determined at 213, the measured board outline can also be plotted on MAX-GRAPH as indicated at 215. This measured board outline is established by routine which locates the edges of the board from the gray-scale values of the image stored in Capture ROI.

Next, if a hit table has been made available in the queue as determined at 217, the total number of hits for the panel is determined at 219. This count is the count of the number of pixels for which the gray-scale value exceeded any of the four thresholds. If this total hit count exceeds a preselected value, as determined at 221, the panel is rejected. Otherwise, proximate hits are associated into blobs and the number of hits in each blob is calculated as determined at 223. The size of the largest blob is then determined at 225 and if this largest blob size exceeds a threshold, the reject flag is set at 229. The hits are then plotted on the MAX-GRAPH superimposed on the outline of the panel as indicated at 231. The memory is then released at 233 for receiving new hit table data from the FEATUREMAX as indicated at 233 and the results are logged on the printer at 235. This loop is repeated as long as the microprocessor remains in the inspection mode.

Figure 9A:
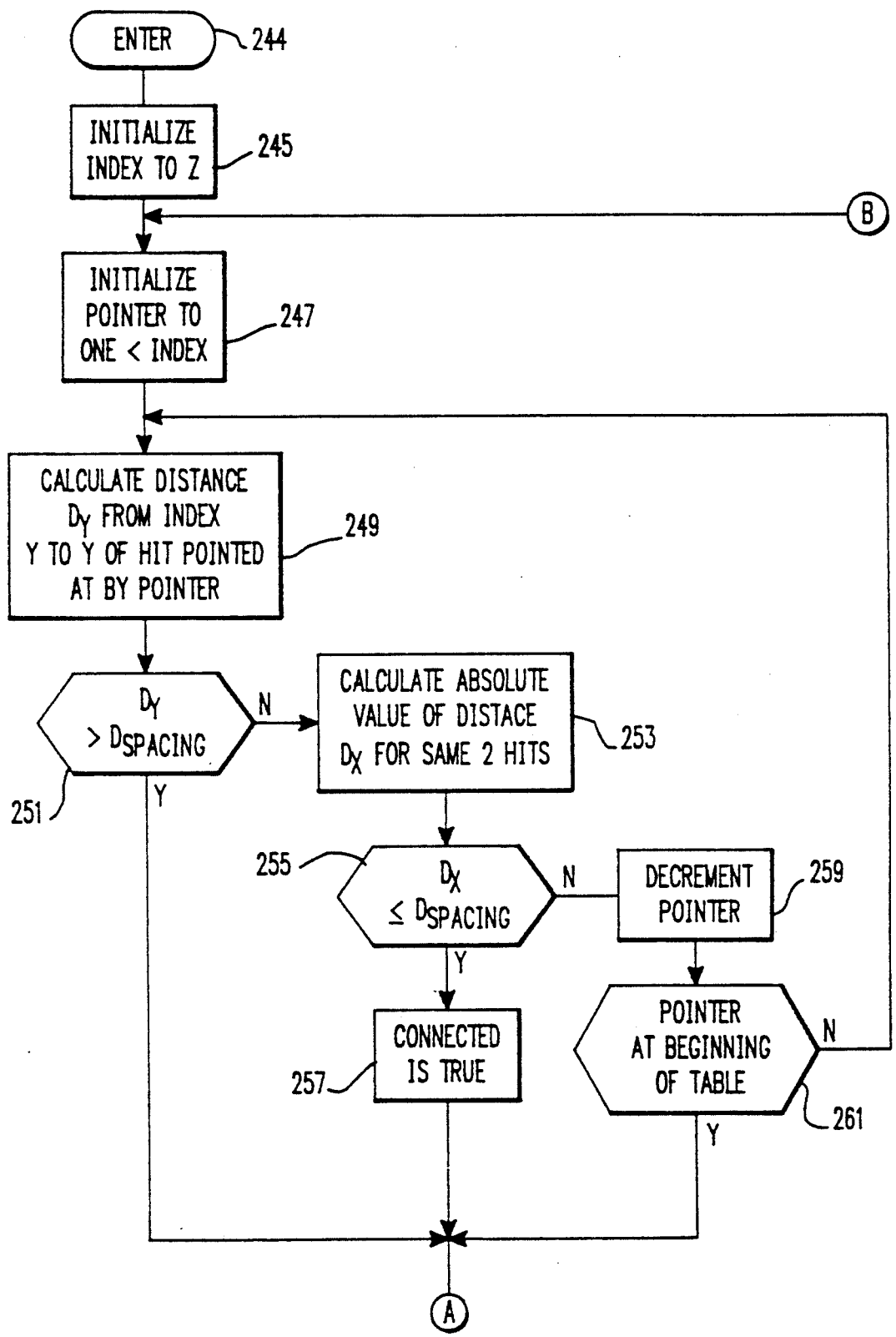
Figure 9B:
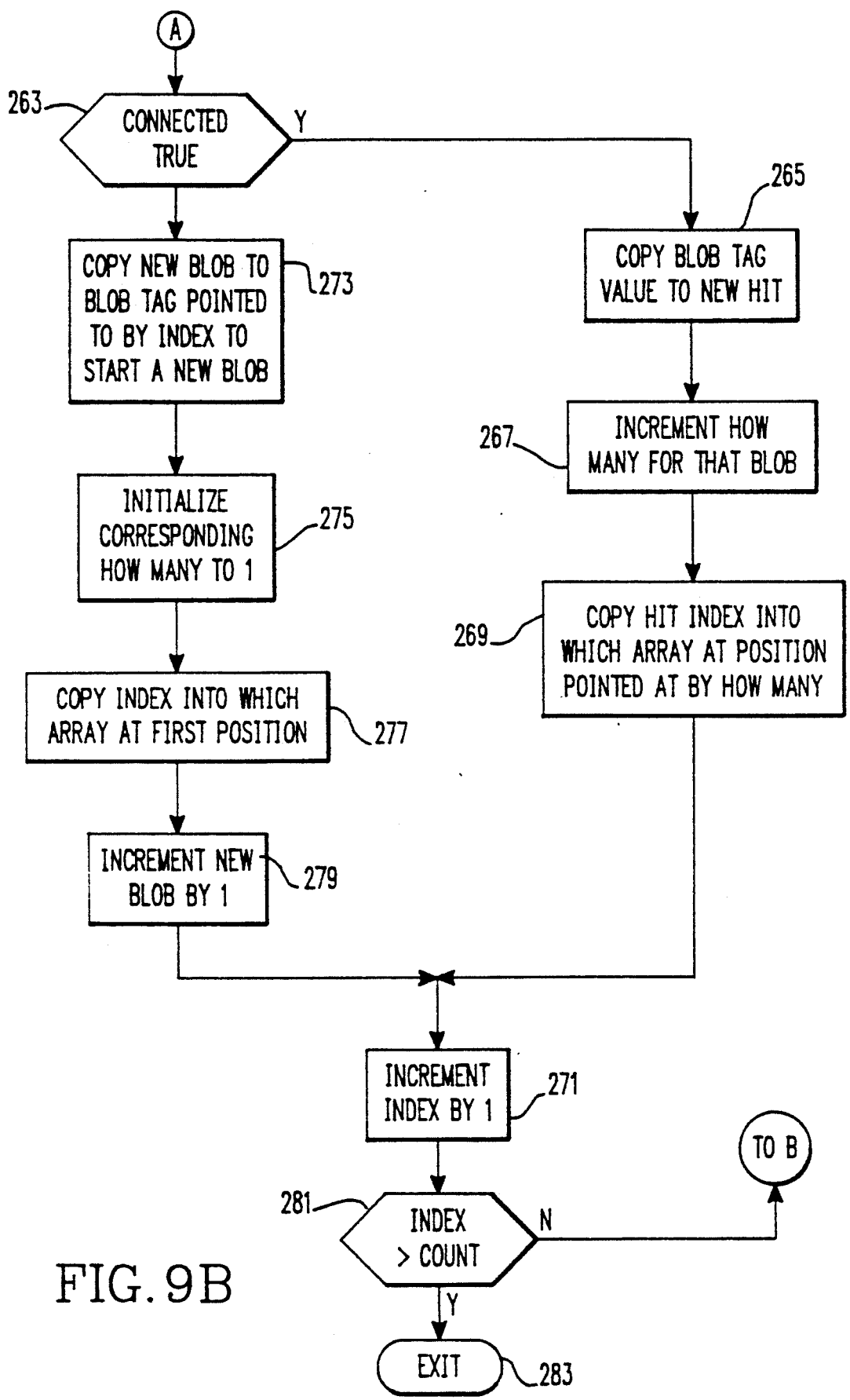
Figure 10:
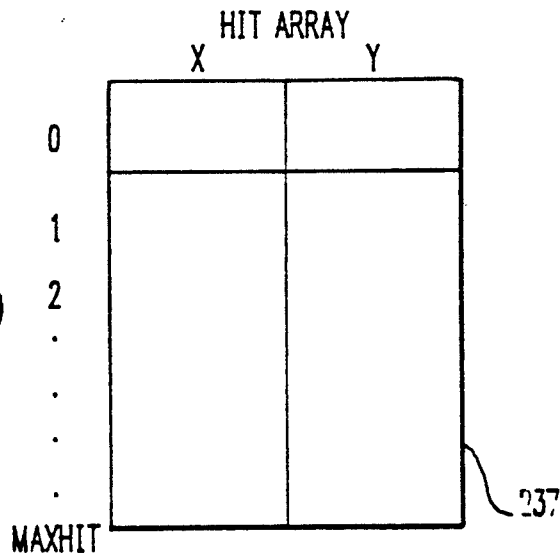
FIGS. 10-12 are diagrams of arrays utilized by the programs described in FIGS. 5 through 8 and 9a and 9b.
Figure 11:
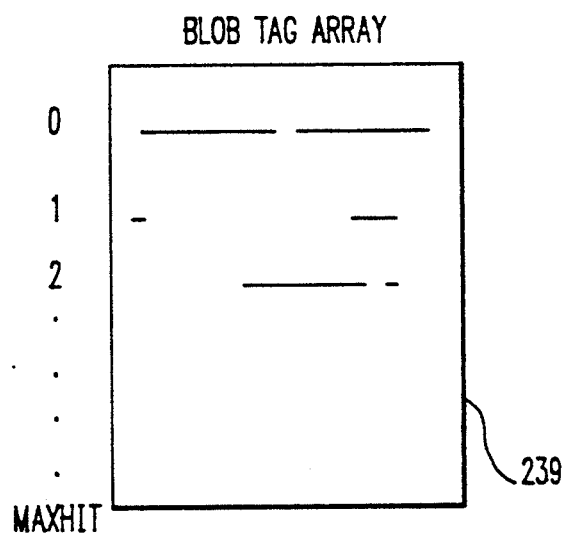
Figure 12:
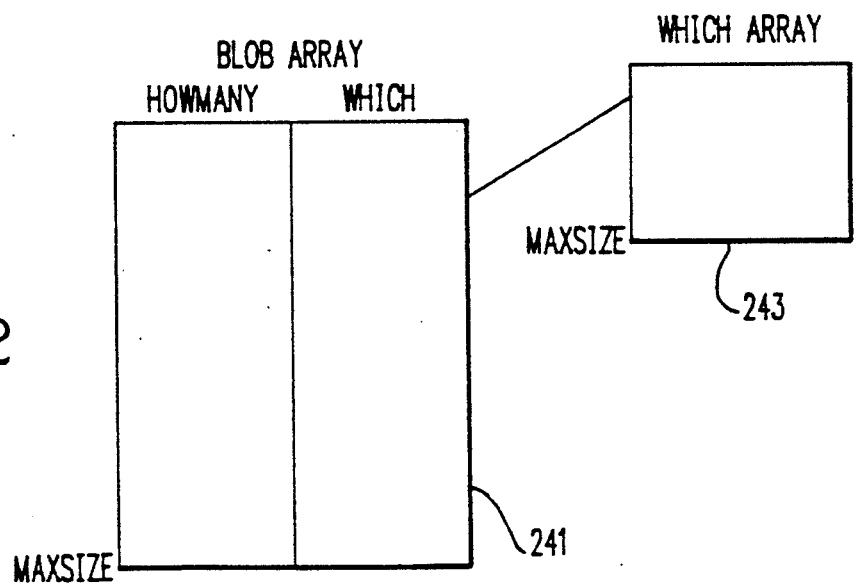

The flow chart for the routine for associating proximate hits into blobs and calculating the number of hits in each blob is illustrated in FIG. 9a and 9b. Data structures used by this routine are illustrated in FIGS. 10 through 12. FIG. 10 illustrates the hit array 237 in which the hits are sequentially numbered and their x and y coordinates are stored. Up to a maximum number of hits can be stored in the array. This max number of hits corresponds to the maximum number of pixels exceeding a threshold that can be tolerated. The blob tag array 239 of FIG. 11 indicates the identification of a blob, if any, with which each of the numbered hits has been associated. The blob array 241 shown in FIG. 12 lists for each identified blob the number of hits associated with the blob and the identification of "which" hits are associated with the blob. The "which" entry 243 has been expanded in FIG. 12 to show that it can include the identification of a number of hits up to a maximum size for the blob. If any panel has a blob with the maximum number of hits in it, the panel is rejected.

Returning to FIGS. 9a and 9b, a parameter INDEX which points to a hit of interest is initialized to two at 245. This starts the processing with the second set of x, y coordinates in the hit array. Another pointer identified as POINTER is set to one less than INDEX as indicated at 247. Next, the distance $D_y$ from the y value of the hit pointed to by INDEX to the y value of the hit pointed to by POINTER is calculated in 249. If this distance, $D_y$ is not greater than a maximum allowable distance between hits associated into a blob, $D_{spacing}$ as determined at 251, then the absolute value of the distance, $D_x$ for the same two hits is calculated at 253. If $D_x$ is less than or equal to $D_{spacing}$ as determined at 255, then a flag CONNECTED is set to true at 257 indicating that the hits pointed to by INDEX and POINTER are close enough to be associated in a blob. If the x spacing is too great to associate the hits into a blob, POINTER is decremented at 259 to move backward through the hit table and the proximity test is repeated until the hit of interest has been evaluated with respect to all of the earlier hits in the hit table as determined at 261.

When the hit selected by the pointer INDEX has been evaluated with regard to all of the previously entered hits in the hit table and the hit was within the parameters set for proximity as indicated by the true condition of the CONNECTED flag at 263 on FIG. 9b, the blob tag for the blob with which the hit is associated is entered at 265 in the blob tag array. The "how many" value for that blob in the blob array is then incremented at 267, and the hit indicated by INDEX is entered into the "which" array at the position pointed at by "how many" as indicated at 269. The pointer INDEX is then incremented by one at 271. If the hit was not close enough to previously enter hits to be associated with any of them into a blob, so that the CONNECTED, flag is not set at 263, then a new blob is indicated at 273 in the blob tag table for the hit pointed to by INDEX and the corresponding "how many" entry in the blob array is initialized to one at 275. The hit pointed to by INDEX is then copied into the "which" array at the first position for the new blob as indicated at 277. NEW BLOB is then incremented by one at 279 for the next blob and INDEX is incremented at 271 to select the next hit in the hit array. If all of the hits in the hit table has not yet been evaluated as determined at 281, the program loops back to 247, otherwise the routine is exited at 283.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A vision system for inspecting a part having a substantially flat reflective surface, said system comprising:
    optical data acquisition means including:
        light source means directing light at the substantially flat reflective surface, and
        camera means generating pixel gray-scale values for light from said light source means reflected from said flat reflective surface; and
    vision processor means comprising:
        storage means storing a pixel array of gray-scale values generated by said camera means;
        an image processing board processing said pixel gray-scale values to identify from said gray-scale values pixels meeting preselected criteria, said image processing board having a frame size covering an array of pixels smaller than the pixel array stored in said storage means;
        transfer means successively transferring to said image processing board for processing, gray-scale values for successive frame sized sections of the pixel array of the storage means until the gray-scale values for all of the pixels of said pixel array have been processed by the image processing board, and wherein said transfer means includes means transferring to said image processing board gray-scale values only for sections of the pixel array of said storage means corresponding to a portion of the substantially flat reflective surface which is more than a predetermined distance inside the edges of said part; and
        processing means evaluating said identified pixels and generating an output based thereon.

2. The system of claim 1 wherein said transfer means includes means overlapping said frame sized sections of the pixel array of the storage means transferred to said image processing board when said portion of said substantially flat reflective surface more than a predetermined distance from the edges of the part is not a whole multiple of said frame size of said image processing board, but only to the extent necessary to only transfer frame sized sections of all the pixel array within said portion of the flat reflective surface more than a predetermined distance from the edges of the part, and including means eliminating double inclusion of identified pixels in overlapping portions of the pixel array processed by the image processing board.

3. The system of claim 2 adapted for inspecting a panel having first and second substantially flat reflective surfaces and including first and second optical data acquisition means generating a first set of pixel gray-scale values for light reflected from the first substantially flat reflective surface of said panel and generating a second set of gray-scale values for light reflected from the second flat reflective surface of said panel, and wherein said vision processor means includes first storage means storing a first pixel array of the first set of pixel gray-scale values and a second storage means storing a second pixel array of the second set of pixel gray-scale values, and wherein said transfer means includes means successively transferring frame sized sections of one pixel array to said image processing board to identify pixels with gray-scale values below the selected threshold and then successively transferring frame sized sections of the other pixel array to said image processing board for identifying pixels having gray-scale values below said selected threshold, and wherein said processing means evaluates the identified pixels from both said first and second pixel arrays.

4. The system of claim 2 wherein defects in said substantially flat reflective surface have a lower reflectivity than said surface, and wherein said image processing board identifies pixels having gray-scale values which fall below a selected threshold.

5. The system of claim 4 wherein said vision processor means includes filter means amplifying differences in magnitude of said gray-scale values to increase contrast in said gray-scale values transferred to said image processing board and to reduce the number of pixels identified by said image processing board which fall below said selected threshold, and wherein said processing means includes means generating a reject signal when the number of identified pixels exceeds a predetermined number.

6. The system of claim 5 wherein said processing means includes proximity associating means associating identified pixels into blobs and means generating a reject signal when a blob contains at least a preselected number of identified pixels.

7. A vision system for inspecting a part having a substantially flat reflective surface, said system comprising:
   optical data acquisition means including:
     light source means directing light at the substantially reflective surface;
     camera means generating pixel gray-scale values for light from said light source means reflected from said flat reflective surface; and
   vision processor means comprising:
     storage means storing a pixel array of gray-scale values generated by said camera means;
     an image processing board comparing said gray-scale values of said pixels with multiple thresholds and identifying as hits pixels which breach each threshold in said pixel array with predetermined gray-scale values; and
     processing means associating pixels identified as hits which are within a predetermined number of pixels of another identified pixel into a blob, said processing means weighting hits included in a blob dependent upon the thresholds breached and generating a reject signal based upon the weighted number of pixels in a blob.

8. The system of claim 7 wherein said vision processor means includes filter means amplifying difference in magnitude of said gray-scale values to increase contrast in said gray-scale values transferred to the image processing board and to reduce the number of pixels identified by said image processing board which fall below said selected threshold.

9. The system of claim 7 wherein said processing means also includes means generating a reject signal when the total number of hits exceeds a selected value.

10. The system of claim 7 including means limiting pixels processed by said image processing board to pixels within said substantially flat surface of said part.

11. The system of claim 7 wherein said vision processing means includes filter means amplifying differences in magnitude of said gray-scale values to increase contrast in said gray-scale values processed by said image processing board and to reduce the number of pixels identified by said image processing board as hits which fall below said selected threshold.

12. The system of claim 11 wherein said vision processing means includes means limiting pixels processed by said image processing board to pixels within said substantially flat surface of said part.

13. The system of claim 12 wherein said processing means also generates a reject signal when the total number of hits exceeds a selected value.

14. The system of claim 7 wherein said part is a panel having two substantially flat reflective surfaces and including first optical data acquisition means generating a first set of pixel gray-scale values for light reflected from the first reflective surface of said panel and a second optical data acquisition means generating a second set of pixel gray-scale values for light reflected from the second reflective surface of said panel, and wherein said vision processor means include first storage means storing a first pixel array of the first set of pixel gray-scale values and second storage means storing a second pixel array of the second set of pixel gray-scale values and including queuing means sequentially transferring data from the first and second storage means for processing by said image processing board, wherein said image processing board identifies hits for each of said first and second pixel arrays, and wherein said processing means associates hits for each of said pixel arrays into blobs, weights the hits in each blob, and generates a reject signal based upon the weighted number of hits in a blob.

15. The system of claim 7 wherein said image processing board has a frame size covering an array of pixels smaller than the pixel array stored in the storage means and wherein said vision processing means includes transfer means successively transferring to said image processing board for processing, gray-scale values for successive frame sized sections of the pixel array of the storage means until the gray-scale values for all of the pixels for said part have been processed by said image processing board.

16. The system of claim 15 wherein said transfer means only transfers gray-scale values to said image processing board for pixels more than a predetermined distance inside the edges of said substantially flat surface of said part.

17. The system of claim 16 wherein said transfer means includes means overlapping said framed sized sections of the pixel array of the storage means transferred to said image processing board when the frame size of the image processing board is not a whole multiple of the portion of the pixel array covering the substantially flat surface of said part, and including means eliminating double inclusion of hits in overlapping portions of the said sections of the pixel array.

* * * * *